United States Patent [19]

Ferres

[11] 4,081,546

[45] Mar. 28, 1978

[54] 3-SUBSTITUTED AMINOCYCLOALKYL ESTERS OF PENICILLIN ANTIBIOTICS

[75] Inventor: Harry Ferres, Horsham, England

[73] Assignee: Beecham Group Limited, United Kingdom

[21] Appl. No.: 807,977

[22] Filed: Jun. 20, 1977

[30] Foreign Application Priority Data

Jun. 24, 1976 United Kingdom ............... 26320/76

[51] Int. Cl.$^2$ .................... A61K 31/43; C07D 499/68; C07D 499/46; C07D 499/32
[52] U.S. Cl. ................................. 424/271; 260/239.1
[58] Field of Search ..................... 260/239.1; 424/271

[56] References Cited

U.S. PATENT DOCUMENTS

| 2,650,218 | 8/1953 | McDuffie et al. ................. 260/239.1 |
| 3,652,546 | 3/1972 | Cheney et al. .................... 260/239.1 |

FOREIGN PATENT DOCUMENTS

| 675,422 | 7/1952 | United Kingdom .............. 260/239.1 |
| 727,481 | 4/1955 | United Kingdom .............. 260/239.1 |

Primary Examiner—Gerald A. Schwartz
Attorney, Agent, or Firm—Jacobs & Jacobs

[57] ABSTRACT

A class of substituted aminocycloalkyl esters of penicillins have improved pharmacokinetic properties and are hydrolysed to the antibacterially active penicillin.

8 Claims, No Drawings

3-SUBSTITUTED AMINOCYCLOALKYL ESTERS OF PENICILLIN ANTIBIOTICS

This invention relates to β-lactam antibiotics and in particular to a class of esters of penicillins which have improved pharmacokinetic properties and are hydrolysed to the antibacterially active penicillin. Individual compounds within the class are useful for veterinary use, for example in the treatment of mastitis in cattle and/or as therapeutic agents for poultry and animals, including man, some of the compounds being absorbed into the bloodstream upon oral administration.

According to the present invention there is provided a penicillin ester of formula (I) or a pharmaceutically acceptable acid addition salt thereof:

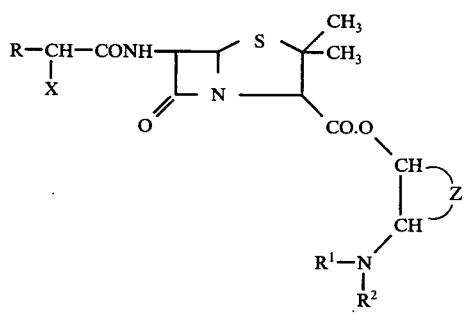

wherein $R^1$ and $R^2$ are the same or different and each represents a $C_{1-6}$ alkyl group or $R^1$ and $R^2$ taken together with the nitrogen atom to which they are attached form a 5- or 6-membered ring; Z represents an optionally substituted straight or branched, saturated or unsaturated divalent hydrocarbon radical; X represents hydrogen, amino, carboxy, alkoxycarbonyl phenoxycarbonyl alkylphenoxycarbonyl or indanyl; R represents phenyl optionally substituted with hydroxy or halogen, phenoxy optionally substituted with, $C_{1-6}$ alkoxy, pyridyl, tetrazolyl or 2- or 3-thienyl, or the group RCHX represents phenyl optionally substituted with $C_{1-6}$ alkoxy; naphthyl optionally substituted with $C_{1-6}$alkoxy or isoxazolyl optionally substituted with halogen or $C_{1-6}$alkyl.

Acid addition salts of the compounds of formula (I) may be formed on the nitrogen atom in the ester moiety or on the nitrogen atom present where X is amino. Suitable acid addition salts include for example, inorganic salts such as the sulphate, nitrate, phosphate and borate; hydrohalides e.g. hydrochloride, hydrobromide, and hydroiodide; and organic acid addition salts such as acetate, oxalate, tartrate, maleate, citrate, succinate, benzoate, ascorbate, methanesulphonate, p-toluenesulphonate, and trifluoroacetate.

A preferred acid addition salt is the hydroiodide.

Suitable examples of alkyl groups for $R^1$ and $R^2$ include methyl, ethyl, n- and iso-propyl, and n-, iso-, sec- and tert-butyl. Preferably, $R^1$ and $R^2$ are the same and are both methyl or ethyl groups. When $R^1$ and $R^2$ complete a heterocyclic ring, they preferably comprise an alkylene chain optionally interrupted with an oxygen or nitrogen atom. Suitable rings include the following;

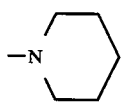 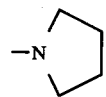

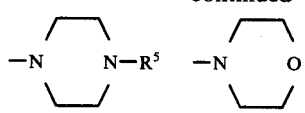

(wherein $R^5$ is hydrogen or alkyl).

The divalent group Z may be for example a $C_2$-$C_5$alkylene or alkenylene group, optionally substituted by $C_1$-$C_6$alkyl, $C_1$-$C_6$alkoxy or halogen. Examples of Z include propylene, butylene, propenylene, butenylene, and butadienylene. Preferably, the group Z, together with the two carbon atoms to which it is attached, forms a 6-membered ring.

Specific examples of the side chain group R.CHX.CONH— which may be present in the compounds of this invention include 2- or 3-thienylacetamido, 4-pyridylacetamido, 2-amino-p-hydroxyphenylacetamido, 1-tetrazolylacetamido, 2,6-dimethoxybenzamido, 3-phenyl-5-methyl-4-isoxazolylcarbonylamino, 3-(2',6'dichlorophenyl)-5-methyl-4-isoxazolylcarbonylamino, 3-(2'-chloro-6'-fluorophenyl)-5-methyl-4-isoxazolylcarbonylamino, 2-carboxyphenylacetamido, 2-phenoxycarbonylphenylacetamido 2-carboxythien-2-ylacetamido.

Preferably, the group R.CHX.CONH— is phenylacetamido, 2-aminophenylacetamido, 2-amino-p-hydroxyphenylacetamido, 2,6-dimethoxybenzamido, or 3-(2'-chlorophenyl)-5-methyl-4-isoxazolylcarbonylamino.

Specific compounds falling within the formula (I) include:

2-N,N-Dimethylaminocyclohexanyl benzylamido penicillanate hydroiodide;
2-N,N-Dimethylaminocyclohexanyl 2,6-dimethoxy benzamido penicillanate, hydroiodide;
2-N,N-Dimethylaminocyclohexanyl 3-(2'-chlorophenyl)-5-methylisoxazolyl-4-carboxamido penicillanate, hydroiodide.

The esters of this invention may be prepared by esterification of the carboxyl group of the corresponding penicillanic acid.

Thus the invention also provides a process for the preparation of compounds of formula (I) which process comprises reacting a compound of formula (V):

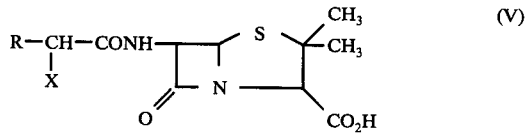

or a reactive esterifying derivative thereof, in which formula R and X are as defined with respect to formula (I) above, with a compound of formula (VI):

or a reactive esterifying derivative thereof, in which formula Z, $R^1$ and $R^2$ are as defined in formula (I).

By the term "reactive esterifying derivative" in relation to compounds (V) and (VI) above, we mean derivatives of (V) and (VI) which when reacted together take part in a condensation reaction with the consequent formation of an ester linkage:

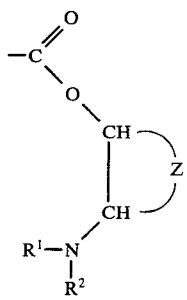

Many methods of esterification using several different combinations of reactive esterifying derivatives are known from the literature. For example, the esterification reaction defined above may be achieved by reacting an activated ester of compound V with the alcohol VI. Preferred activated ester groups are mixed anhydrides, but other activated ester groups include the acid halide, e.g. acid chloride, and the reactive intermediate formed with a carbodiimide or carbonyldiimidazole.

Alternatively compound V or a salt thereof, preferably the sodium, potassium or triethylammonium salt, may be reacted with a halide, alkylsulphonyl (e.g. methansulphonyl) or arylsulphonyl (e.g. p-toluenesulphonyl) ester of compound (VI).

The reaction is generally carried out in an inert organic solvent.

When the side-chain group of compound (V) contains a reactive group such as a free amino, hydroxyl, or carboxy group, it is preferable that the group should be protected prior to the esterification reaction. Such protected groups should be capable of being cleaved by methods sufficiently mild to avoid destruction of the molecule at the ester group or at the β-lactam ring.

Hydroxy groups may be protected by generally known methods for example by etherification or acylation, and a carboxylic acid group can be protected by esterification.

Examples of protected amino groups include the protonated amino group ($NH^+_3$) which after the acylation reaction can be converted to a free amino group by simple neutralisation; the benzyloxy-carbonylamino group or substituted benzyloxycarbonyl-amino groups which are subsequently converted to $NH_2$ by catalytic hydrogenation; and various groups which after the acylation reaction regenerate the amino group on mild acid hydrolysis, such as t-butyloxycarbonyl group which may be removed by treatment with trifluoroacetic acid, hydrogen chloride, or p-toluenesulphonic acid.

Another example of a protected amino group which may subsequently be converted to $NH_2$ by mild acid hydrolysis include groups of formula (VII):

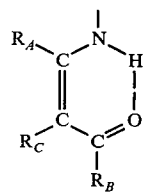

(VII)

wherein $R_A$ is alkyl, aralkyl or aryl group, $R_B$ is an alkyl, aralkyl, aryl, alkoxy, aralkoxy or aryloxy group, and $R_C$ is a hydrogen atom or an alkyl, aralkyl, or aryl group, or $R_c$ together with either $R_A$ or $R_B$ completes a carbocyclic ring.

An example of a "protected amino" which can be converted to $NH_2$ after the N-acylation reaction is the azido group. In this case, the final conversion into $NH_2$ may be brought about by either catalytic hydrogenation or electrolytic reduction.

Alternatively, the amino group may be blocked at the nitro group which is later converted to the amino group by reduction. Other protected amino groups include the β,β,β,-trichloroethoxycarbonylamino radical, which may be removed by reduction with zinc in acetic acid.

An alternative method of making compounds of this invention is by N-acylation of the corresponding 6-aminopenam.

Thus, in another of its embodiments, this invention provides a method for the preparation of compounds of formula (I) which method comprises reacting a compound of formula (VIII):

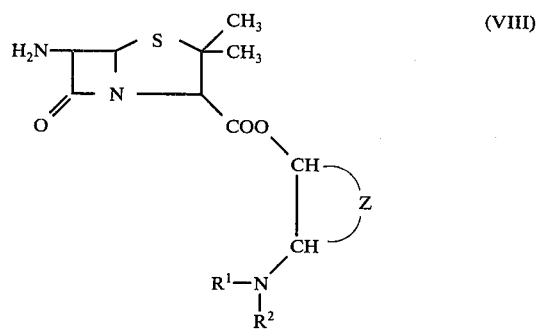

(VIII)

or a N-protected derivative thereof with a reactive derivative of a compound of formula (IX):

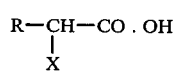

(IX)

wherein R and X are as defined above, in which any reactive groups may be blocked; and thereafter, if necessary, removing any blocking groups in the side-chain group and removing any N-protecting groups.

Examples of "N-protected derivatives" of compound (VIII) include N-silyl and N-phosphorylated derivatives.

By the term "N-silyl derivative" of compound (VIII), we mean the product of reaction of the amino group of compound (VIII) with a silylating agent such as a halosilane or a silazane of the formula:

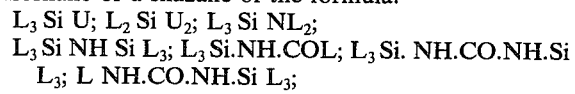

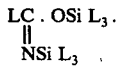

wherein U is a halogen and the various groups L which may be the same or different, each represents hydrogen or alkyl, alkoxy, aryl, or aralkyl. Preferred silylating agents are silyl chlorides, particularly trimethylchlorosilane, and dimethyldichlorosilane.

The term "N-phosphorylated" derivative of compound (VIII) is intended to include compounds wherein the 6-amino group of formula (VIII) is substituted with a group of formula:

wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

A reactive derivative of compound (IX) is employed in the above process. The choice of reactive derivative will of course be influenced by the chemical nature of the substituents of the acid.

Suitable derivatives of the acid (IX) include an acid halide, preferably the acid chloride or bromide. Acylation with an acid halide may be effected in the presence of an acid binding agent for example a tertiary amine (such as triethylamine or dimethylaniline), an inorganic base (such as calcium carbonate or sodium bicarbonate) or an oxirane, which binds hydrogen halide liberated in the acylation reaction. The oxirane is preferably a ($C_{1-6}$)-1,2-alkylene oxide - such as ethylene oxide or propylene oxide. The acylation reaction using an acid halide may be carried out at a temperature in the range −50° to +50° C, preferably −20° to +30° C, in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (IX) or a salt thereof with a halogenating (e.g. chlorinating or brominating) agent such as phosphorus pentachloride, thionyl chloride or oxalyl chloride.

Alternatively, the N-acylating derivative of the acid (IX) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphorous acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IX) are the acid azide, or activated esters such as esters with 2-mercapto-pyridine, cyanomethanol, p-nitrophenol, 2,4-dinitrophenol, thio-phenol, halophenol, including pentachlorophenolllmonomethoxyphenol or 8-hydroxyquinoline; or amides such as N-acylsaccharins or N-acylnaphthalimides; or an alkylidene iminoester prepared by reaction of the acid (IX) with an oxime.

Some activated esters, for example the ester formed with 1-hydroxybenztriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (IX) include the reactive intermediate formed by reaction in situ with a condensing agent such as a carbodiimide, for example N,N-diethyl-, dipropyl- or diisopropylcarbodiimide, N,N'-di-cyclohexylcarbodiimide, or N-ethyl-N'-γ-dimethylaminopropylcarbodiimide; a suitable carbonyl compound, for example N,N'-carbonyldiimidazole or N,N'-carbonylditriazole; an isoxazolinium salt, for example N-ethyl-5-phenylisoxazolinium-3-sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3$—$C_6H_6$); or a phosphoric acid condensing agent such as diethylphosphorylcyanide. The condensation reaction is preferably carried out in an organic reaction medium, for example methylene chloride, dimethylformamide, acetonitrile, alcohol, benzene, dioxan, or tetrahydrofuran.

A third method for the preparation of compounds of formula (I) comprises:

(a) reacting a compound of formula (I) above, wherein the side-chain group R.CHX.CONH— has the heretofore stated meaning and represents the side-chain of a natural penicillin to form an imino bond on the 6-amino atom;

(b) reacting the resulting compound to introduce a group $QR_f$ on the imino carbon atom, wherein Q is oxygen, sulphur or nitrogen and $R_f$ is an alkyl group of from 1 to 12 carbon atoms, or an aralkyl group of from 5 to 14 carbon atoms, to form an iminoether, iminothioether or amidine (when Q is O, S or N respectively);

(c) reacting with a reactive derivative of an acid of formula (IX) above (d) treating with water or an alcohol; and (e) thereafter if necessary removing any blocking groups in the side-chain group.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The compositions may be formulated for administration by any route, such as oral, topical or parenteral. The compositions may be in the form of tablets, capsules, powders, granules, lozenges, creams of liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous of oily suspensions, solutions, emulsions, syrups, or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg. of the active ingredient. The dosage as employed for adult human treatment will preferably range from 100 to 3000 mg. per day, for instance 1500 mg. per day, depending on the route and frequency of administration.

The ester of formula (I) may be the sole therapeutic agent in the compositions of the invention or a combination with other antibiotics may be employed. Advantageously the compositions also comprise a compound of formula (XI) or a pharmaceutically acceptable salt or ester thereof:

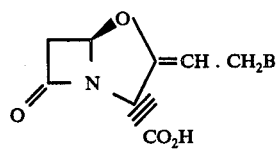

wherein B is hydrogen or hydroxyl.

Preferably the compound of formula (XI) is clavulanic acid of formula (XII) or a pharmaceutically acceptable salt or ester thereof;

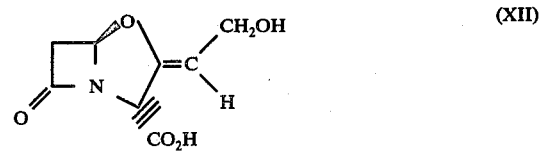

The preparation of these compounds is described in Belgium Pat. Nos. 827,926, 836,652 and West German Offenlegungsschrift No. 2,616,088.

It will be clear that the side-chain of the esters of formula (I) may contain one or more potentially asymmetric carbon atoms. This invention includes all the possible epimers of compounds (I) as well as mixtures of them.

The following Examples illustrate the preparation of some of the compounds of this invention.

General Procedure used in all cases for synthesising the penicillin esters of Example 1–3

The penicillin salt (0.01M) was suspended in dry methylene dichloride (75 ml) at $-10°$ to $-15°$ C and treated with isobutylchloroformate (1.36g., 0.01M) and 2–3 drops of pyridine. After stirring at $-10°$ to $-15°$ C for 20 minutes the reaction mixture was cooled to $-20°$ C and filtered. The aminoalcohol (0.01M) in methylene dichloride (25 ml) was added to the filtrate, maintaining the temperature at $-10°$ C during addition. Stirring was continued for 2–3 hours without external cooling. After evaporation of the solvent the residual oil was dissolved in ethyl acetate (100 ml) and washed with water (2 × 100 ml). The solution was dried over anhydrous magnesium sulphate and evaporated to an oil. The hydroiodide salt of the penicillin ester was prepared by forming a solution of the free base oil in acetic acid (ca 2 ml) and water (10 –15 ml) at 0° C and treating this with a solution of sodium iodide (2.0g) in water (1 ml). After stirring at 0° C for 15 minutes the precipitating gum was washed with water and dissolved in methylene dichloride (10–15 ml), dried over anhydrous magnesium sulphate, concentrated to about one fifth its volume and added to anhydrous diethyl ether with stirring at 0° C to precipitate the product as a white amorphous hydroiodide salt.

EXAMPLE 1

2-N,N-Dimethylaminocyclohexanyl Benzylamido Penicillanate, Hydroiodide

Scale: 0.01M. Yield of product: 2.71g; 46%.

$\nu$max (KBr) 3400 (br.), 1778, 1742, 1663, 1510, 1300, 1255, 1202 and 1184 cm$^{-1}$, $\delta[(CD_3)_2SO]$ 1.48 (s) and 1.63 (s) (gem-dimethyls), 1.0–2.3 ((CH$_2$)$_4$), 2.75 (d) (NMe$_2$), 3.58 (Ph C$\underline{H}_2$), 4.48 (s) and 4.77 (s) (C3proton equimolar mixture of isomers) 5.4–5.7 (m) ($\beta$-lactams), 7.30 (m) (C$_6$H$_5$), 8.85 (d) (CONH), biochromatogram (B/E/W) Rf0.74.

EXAMPLE 2

2-N,N-Dimethylaminocyclohexanyl 2,6-Dimethoxybenzamido Penicillanate, Hydroiodide Scale: 0.01M. Yield of product: 2.78g; 44%.

$\nu$max (KBr) 3400 (br.), 1775, 1738, 1660, 1592, 1470, 1252 and 1104 cm$^{-1}$, $\delta$ [CDCl$_3$] 1.62 (s) and 1.73 (s)

(gemdimethyls, 1.0–2.7 ((CH$_2$)$_4$), 2.89 (s) (NMe$_2$), 7.85 (s) (2 × OMe), 4.69 (s) and 5.29 (s) (C3 proton equimolar mixture of isomers), 5.6–6.1 (m) ($\beta$-lactams) 6.61 (d) and 7.34 (m) (C$_6$H$_3$), 8.6 (br.) (CONH), biochromatogram (B/E/W) Rf0.83.

EXAMPLE 3

2-N,N-Dimethylaminocyclohexanyl 3-(2'-Chlorophenyl)-5-Methylisoxazolyl-4-Carboxamido Penicillanate, Hydroiodide Scale: 0.01M. Yield of product: 2.82g; 37%.

m.p. 142°–144° C (dec.) (Found: C, 48.2; H, 4.9; N, 8.1; S, 5.1%. C$_{27}$H$_{34}$ClIn$_4$O$_5$S requires C, 47.1; H, 5.0; N, 8.1; S, 4.7%), $\nu$max (KBr) 3400 (br.), 1780, 1743, 1665, 1598, 1505, 1202 and 1187 cm$^{-1}$, $\delta$ [(CD$_3$)$_2$SO] 1.46 (s) and 1.53 (s) gem-diemthyls) 1.0–2.3 (4 × CH$_2$), 8.67 (s) (CH$_3$), 8.69 (s) (N(CH$_3$)$_2$), 3.0–4.0 (2 × CH), 4.35 (s) and 4.67 (s) (C3 proton equimolar mixture of isomers), 5.4–5.8 ($\beta$-lactams), 7.57 (m) (C$_6$H$_4$), 8.45 (d) (CONH), biochromatogram (B/E/W) Rf0.74.

What we claim is:

1. A penicillin ester of formula (I) or a pharmaceutically acceptable acid addition salt thereof:

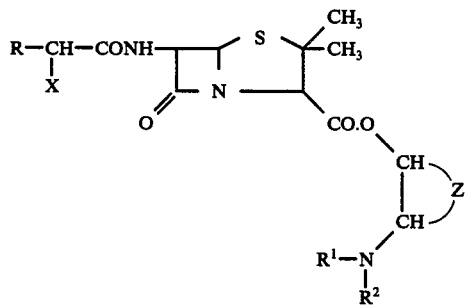

wherein

R$^1$ and R$^2$ are the same or different and each represents a C$_{1-6}$ alkyl group or R$^1$ and R$^2$ taken together represents an alkylene chain optionally interrupted with an oxygen or nitrogen atoms forming a 5- or 6-membered heterocyclic ring;

Z represents an optionally substituted straight or branched saturated or unsaturated divalent hydrocarbon radical wherein the optional substituents are selected from the group consisting of C$_1$-C$_6$ alkyl, C$_1$-C$_6$ alkoxy and halogen;

X represents hydrogen, amino, carboxy, alkoxycarbonyl, phenoxycarbonyl, alkylphenoxycarbonyl or indanyl; R represents phenyenoptionally substituted with hydroxy or halogne; naphthyl optionally substituted with C$_{1-6}$ alkoxy; phenoxy optionally substituted with C$_{1-6}$ alkoxy; 2- or 3-thienyl, pyridyl, tetrazolyl, or the group RCHX represents phenyl optionally substituted with C$_{1-6}$ alkoxy or isoxazolyl optionally substituted with halogen or C$_{1-6}$ alkyl.

2. A penicillin ester as claimed in claim 1 wherein the group Z together with the two carbon atoms to which it is attached, forms a 6-membered ring.

3. A penicillin ester as claimed in claim 1 wherein R$^1$ and R$^2$ are both methyl.

4. A penicillin ester as claimed in claim 1 wherein the side-chain group R.CHX.CONH— represents phenylacetamido, 2-aminophenylacetamido, 2-amino-p-hydroxyphenylacetamido, 2,6-dimethoxybenzamido, or 3-(2'-chlorophenyl)-5-methyl-4-isoxazolylcarbonylamino.

5. 2-N,N-Dimethylaminocyclohexanyl benzylamido penicillanate.

6. 2-N,N-Dimethylaminocyclohexanyl 2,6-Dimethoxy benzamido penicillanate.

7. 2-N,N-Dimethylaminocyclohexanyl 3-(2'-chlorophenyl)-5-methylisoxazolyl-4-carboxamido penicillanate.

8. A pharmaceutical composition for the treatment of penicillin-responsive bacterial infections comprising a penicillin ester as claimed in claim 1 in an antibacterially effective amount together with a pharmaceutically acceptable carrier or excipient.

* * * * *